(12) United States Patent
Haase et al.

(10) Patent No.: US 9,325,548 B2
(45) Date of Patent: Apr. 26, 2016

(54) ELECTRONIC CIRCUIT AND METHOD FOR TRANSMITTING AN ASK SIGNAL

(71) Applicant: Endress + Hauser Conducta Gesellschaft für Mess- und Regeltechnik mbH + Co. KG, Gerlingen (DE)

(72) Inventors: Bjorn Haase, Stuttgart (DE); Stefan Pilz, Geithain (DE)

(73) Assignee: ENDRESS & HAUSER CONDUCTA GESELLSCHAFT FÜR MESS-UND REGELTECHNIK MBH + CO. KG, Gerlingen (DE)

( * ) Notice: Subject to any disclaimer, the term of this patent is extended or adjusted under 35 U.S.C. 154(b) by 0 days.

(21) Appl. No.: 14/608,325

(22) Filed: Jan. 29, 2015

(65) Prior Publication Data

US 2015/0222462 A1 Aug. 6, 2015

(30) Foreign Application Priority Data

Feb. 6, 2014 (DE) .......................... 10 2014 101 502

(51) Int. Cl.
*H04L 27/01* (2006.01)
*H04L 27/04* (2006.01)
*H04W 72/04* (2009.01)
*A61B 8/00* (2006.01)
*A61B 5/103* (2006.01)

(52) U.S. Cl.
CPC ........... *H04L 27/04* (2013.01); *H04W 72/0453* (2013.01); *A61B 5/103* (2013.01); *A61B 8/4472* (2013.01)

(58) Field of Classification Search
CPC ........... G06K 7/10336; G06K 7/10435; H04L 27/04; H04L 27/02; H04L 67/12; H02J 5/005; H04B 10/50; A61M 1/1601; A61B 5/6846; A61B 8/4472; A61B 5/103; A61N 1/37223; H03J 2200/10; H03J 3/20; Y10S 128/903; Y10T 307/615
USPC ......... 375/224, 259, 268, 269, 295, 302, 316, 375/322; 329/347; 332/149, 150
See application file for complete search history.

(56) References Cited

U.S. PATENT DOCUMENTS

2002/0105436 A1* 8/2002 Bell et al. ................. 340/870.17
2013/0003820 A1* 1/2013 Malhan et al. ................ 375/238

*Primary Examiner* — Tesfaldet Bocure
(74) *Attorney, Agent, or Firm* — Bacon & Thomas, PLLC (57) ABSTRACT

An electronic circuit for transmitting an ASK signal, wherein the ASK signal transmits data and energy between a first side having a first interface, and a second side having a second interface corresponding to the first interface. The first interface and the second interface are embodied for transmitting data and energy, and the first interface and the second interface are embodied as galvanically separated interfaces, comprising a converting apparatus for transforming data, especially a digital data signal, into an analog wanted signal; a carrier source for producing a carrier signal having a carrier frequency; a resonator circuit for merging the carrier signal with the wanted signal to form the ASK signal with an amplitude. The resonator circuit is so embodied that it is excited by the carrier signal to execute periodic oscillations, wherein the ASK signal includes the wanted signal and the periodic oscillations, and wherein essentially the wanted signal determines the amplitude of the ASK signal. A measurement circuit for measuring the power of the ASK signal; and a data processing unit, which is so embodied that it controls the transmission of the ASK signal, wherein the controlled variable is the measured power of the ASK signal, and wherein the manipulated variable is the carrier frequency. The invention relates further to a method.

17 Claims, 6 Drawing Sheets

ELECTRONIC CIRCUIT AND METHOD FOR TRANSMITTING AN ASK SIGNAL

TECHNICAL FIELD

The invention relates to an electronic circuit and method for transmitting an ASK signal from a first side to a second side of a measuring device. Besides data, also energy is transmitted.

BACKGROUND DISCUSSION

The problem to which the invention is directed will be explained based on signal transmission between a transmitter-side (in general, a superordinated unit) and a sensor-side (in general, a consumer). The invention can, however, be applied in other systems, where data and energy need to be transmitted.

Usually attached to a transmitter is a cable for connection to a sensor. The cable connection to a sensor occurs frequently via a plugged connection, for example, via a galvanically decoupled, especially inductive, interface. In this way, electrical signals can be transmitted contactlessly. The galvanic isolation leads to advantages as regards corrosion protection, potential isolation, preventing mechanical wear of the plug, etc. Such systems are sold by Endress+Hauser under the mark "Memosens".

The signal to be transferred, i.e. the data (the "information"), must be converted into a suitable format for transmission. In this regard, a so-called carrier signal is changed by the data. This procedure is called "modulation". The opposite procedure, thus the filtering out of data from a carrier signal, is called "demodulation".

Binary transmission of digital signals occurs in the simplest case by using a two state, rectangular signal. In this case, there is a switching between two amplitudes, frequencies or phases. The present invention relates to the use of an amplitude modulation. In the transmission of digital signals, one speaks of keying instead of modulation, in which sense the invention relates to ASK, or amplitude shift keying.

The mentioned inductive interface is usually embodied as a system with two coils, which are, for example, plugged into one another. Typically, both data (in two directions) as well as also energy (from transmitter-side to sensor-side) are transmitted. The energy must, in such case, be large enough that a connected sensor is supplied sufficiently with energy, so that a durable measurement operation is assured.

The challenge of such contactless energy- and data transmission lies, first of all, in the rough operating- and environmental conditions in industrial environments. Because of the environmental conditions (temperature, humidity, etc.), tolerances for the components (tolerances of inductances of the coils, etc.) are especially large. If, for example, assemblies are designed for typical temperatures, with which medical equipment is sterilized (typically above 120° C.), then this means e.g. that the coils experience significantly modified inductance values at high temperatures.

Of concern relative to the tolerances is especially the coupling transformer, which inductively couples the coil on the transmitter-side with the coil on the sensor-side, respectively forms with these two coupled coils a transformer. In the case of this coupling system, the mechanical pairing of the two partner coils is less exactly toleranced than in the case of usual transformers. In other words, this contactless energy- and data transmission system involves very large deviations of the inductive coupling and especially large deviations of the inductance values.

Another challenge in the industrial environment involves power limiting, which enters especially in the case of explosion-protection requirements. Explosion protection requirements mean, for instance, limiting power to below 10 mW.

Moreover, it must be assured that data are transmitted uncorrupted. Two effects must be taken into consideration as error sources for the corruption of data signals.

On the one hand, non-uniformity of the components can lead to corrupted transmissions. If, for example, the inductance value of the coil on the transmitter side is detuned relative to the nominal frequency, significantly higher or significantly lower signal levels, i.e. especially voltage level, result for the data signal, since, among other things, the resonance circuit formed by the coil is detuned. In the one case, there is the danger that the transmitter-side attempts to retrieve on the supply lines more power than is available. In the case of too low signal levels, the transferred energy is insufficient for reliably operating the sensor-side.

On the other hand, it is possible that the amplitude of the alternating signals applied on the transmitter- and sensor-sides can be influenced by load jumps of the sensor. Thus, there results for the case, in which the sensor has for short-times an increased power requirement, the danger that the resulting jumps in signal level are incorrectly interpreted as a communication signal.

SUMMARY OF THE INVENTION

An object of the invention, therefore, is to supply a consumer connected to a superordinated unit reliably with energy, while protecting data communication.

The object is achieved by an electronic circuit. The electronic circuit transmits, via an ASK-signal, data and energy between a first side having a first interface, and a second side having a second interface corresponding to the first interface. The first side corresponds, in such case, to the side of a superordinated unit, e.g. a transmitter; the second side corresponds to the side of a consumer, e.g. a sensor. The first interface and the second interface are embodied for transmitting data and energy, and the first interface and the second interface are embodied as galvanically separated interfaces, especially inductive interfaces. The electronic circuit further includes: a converting apparatus for converting the data, especially a digital, data signal, into an analog, wanted signal; a carrier source for producing a carrier signal with a carrier frequency; a resonator circuit for merging the carrier signal with the wanted signal to form the ASK-signal with an amplitude, wherein the resonator circuit is so embodied that it is excited by the carrier signal to execute periodic oscillations, the ASK-signal includes the wanted signal and the periodic oscillations, and wherein essentially the wanted signal determines the amplitude of the ASK-signal. The electronic circuit further includes a measurement circuit for measuring the power of the ASK-signal; and a data processing unit, which is so embodied that it controls the transmission of the ASK-signal, wherein the controlled variable is the measured power of the ASK-signal, and wherein the manipulated variable is the carrier frequency.

Thus, a constant power is transmitted. This is achieved by using the carrier frequency as manipulated variable. If the measured power is used as controlled variable, it is possible to control out the unavoidably arising tolerances of the interfaces, the positioning of the interfaces relative to one another and the disturbances in the environment.

In an advantageous embodiment, the data processing unit is embodied as a carrier source, this saves space. The data processing unit can undertake a number of tasks, so that programming effort and the need for additional hardware components is kept small. For example, the data processing unit can undertake both control as well as also data processing as well as also carrier frequency generation and by calculation ascertain a power value e.g. by multiplying a digitally converted voltage value and a digitally converted electrical current value.

Preferably, the data processing unit suspends control action while data is being sent. During the transmitting of data, no reliable power measurement is possible. Additionally, in this way it can be excluded that during an ongoing communication a control attempt leads to an undesired amplitude modulation, which could be interpreted incorrectly by the second side.

In an advantageous embodiment, the setpoint of the controlled variable, power, is variable. Thus, for instance, depending on operating mode, the system can be controlled to another power. An operating mode, "memory erase", "firmware change" or the like, can, for example, require a higher power.

In a preferred further development, the converting apparatus is embodied as an amplifier and the data, especially the data signal, determines the amplification. Thus, a greater amplification means, for instance, a digital "1", while a lesser amplification means a digital "0". A linear amplifier can be used as amplifier. Alternatively, a class-D amplifier can be provided. Also, an amplifier as presented in the U.S. publication application U.S. 2014/0097898 can be used.

In an alternative further development, the converting apparatus is embodied as a load modulation circuit with at least one switch means and at least one impedance addable by the switch means. In such case, the data, especially the data signal, determines the switch closing of the switching means. This represents a comparatively simple circuit. In given cases, an amplifier is supplementally provided, which delivers the required power.

In the case of both alternatives, the amplitude of the ASK-signal to be transmitted changes linearly with the wanted signal. Via a variation of the wanted signal, it is, thus, possible, to achieve a voltage change of the alternating voltage component to be transmitted for the ASK-signal. This effect can be utilized to modulate the data onto the ASK-signal by means of an amplitude modulation.

In an advantageous embodiment, the resonator circuit includes at least one bridge circuit, comprising a half- or full bridge, especially a four quadrant controller; and a series oscillatory circuit, wherein the series oscillatory circuit is connected with the bridge circuit, and wherein the series oscillatory circuit corresponds to the first interface, wherein the wanted signal and the carrier signal are fed to the bridge circuit.

In an alternative embodiment, the resonator circuit includes: at least one parallel oscillatory circuit with an input and an output, wherein the parallel oscillatory circuit corresponds to the first interface; and a switch means, especially a transistor having a gate-connection, a drain-connection and a source-connection, wherein the wanted signal is fed to the input of the parallel oscillatory circuit, wherein the output of the parallel oscillatory circuit is connected with the drain-connection, and wherein the gate-connection is fed the carrier signal.

In an additional alternative embodiment, the resonator circuit includes: at least one parallel oscillatory circuit with an input and an output; a switch element, especially a transistor having a gate-connection, a drain-connection and a source-connection; and a series oscillatory circuit, wherein the series oscillatory circuit corresponds to the first interface, wherein the wanted signal is fed to the input of the parallel oscillatory circuit, wherein the output of the parallel oscillatory circuit is connected with the drain-connection, wherein the series oscillatory circuit connects the drain-connection with the source-connection, and wherein the gate-connection is fed the carrier signal.

Common to all of the described embodiments of the resonator circuit is that, by changing the carrier frequency a voltage amplitude, thus the amplitude of the ASK-signal, applied on the first interface can be changed and, thus, the power transmitted to the second side can be increased or lowered.

The invention relates further to a measuring device, comprising an electronic circuit according to one of the above described embodiments.

In an advantageous form of embodiment, the measuring device includes a superordinated unit, especially a transmitter, and a consumer, especially a sensor, wherein the superordinated unit is connected with the consumer via the first interface and the second interface.

The object is further achieved by a method. The method is suitable for transmitting an ASK-signal between a first side and a second side, wherein the ASK-signal transmits data and energy. The method includes steps as follows: converting the data, especially converting a digital data signal, into an analog wanted signal; producing a carrier signal with a carrier frequency; merging the carrier signal with the wanted signal to form the ASK-signal with an amplitude, wherein periodic oscillations are produced from the carrier signal, wherein the ASK-signal includes the wanted signal and the periodic oscillations, and wherein the amplitude of the ASK-signal is essentially determined by the wanted signal; and transmitting the ASK-signal, wherein the power of the transmission is determined and the transmission of the ASK-signal is controlled, wherein the controlled variable is the measured power of the ASK-signal, and wherein the manipulated variable is the carrier frequency.

If the measured power is used as controlled variable, it is possible to control out unavoidably arising tolerances of the interfaces, the positioning of the interfaces relative to one another and the disturbances in the environment.

In a preferred embodiment, the wanted signal is generated by an amplifier and the amplification is predetermined by the data, especially the data signal.

In an alternative preferred embodiment, the wanted signal is generated by a switchable load and the switching is predetermined by the data, especially by the data signal.

BRIEF DESCRIPTION OF THE DRAWINGS

The invention will now be explained in greater detail based on the appended drawing, the figures of which show as follows.

DETAILED DISCUSSION IN CONJUNCTION WITH THE DRAWINGS

In the figures, equal features are provided with equal reference characters.

Figure 1:
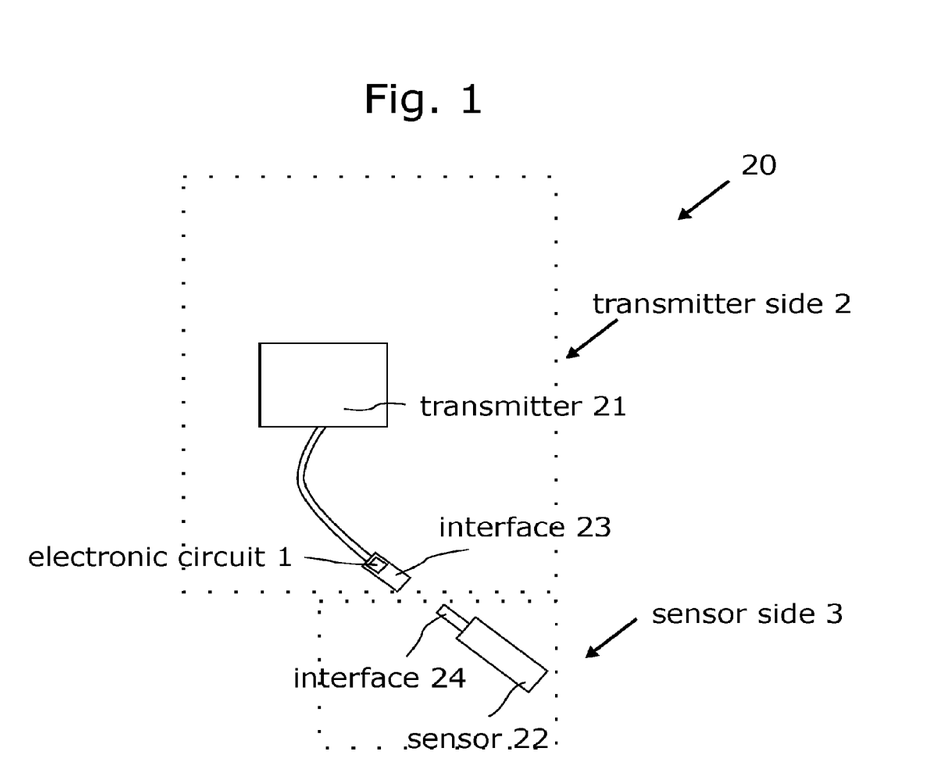
FIG. 1 is a measuring device, in which the circuit of the invention is applied.

First, a measuring device 20 will be explained, in which the electronic circuit of the invention can be applied. Such is shown in FIG. 1. Via an interface 24, a sensor 22 ("sensor-side 3") communicates with a transmitter 21 ("transmitter-side 2"). Provided on the transmitter 21 is a cable, on whose other end is an interface 23 complementary to the first interface 24. The interfaces 23, 24 are embodied as a galvanically separated interfaces, especially as inductive interfaces, which can be coupled with one another by means of a mechanically plugged connection. Transmitted via the interfaces 23, 24 are data (bidirectional) and energy (unidirectional, i.e. from the transmitter 21 to the sensor 22). The measuring device 20 is predominantly applied in process automation. Sensor 20 is thus, for instance, a pH-, redox-potential-, also ISFET-, temperature-, conductivity-, pressure-, oxygen-, especially dissolved oxygen-, or carbon dioxide sensor; an ion-selective sensor; an optical sensor, especially a turbidity sensor, a sensor for optically determining oxygen concentration, or a sensor for determining number of cells and cell structures; a sensor for monitoring certain organic or metal compounds; a sensor for determining a concentration of a chemical substance, for example, a certain element or a certain compound; or a biosensor, e.g. a glucose sensor.

The method of the invention is used for data transmission between transmitter 21 and sensor 22. The circuit of the invention, reference character 1, can be installed, in such case, both in the transmitter 21, in the cable or even in the sensor. Preferably, the electronic circuit is located in the transmitter 21 or in the cable.

Figure 2:
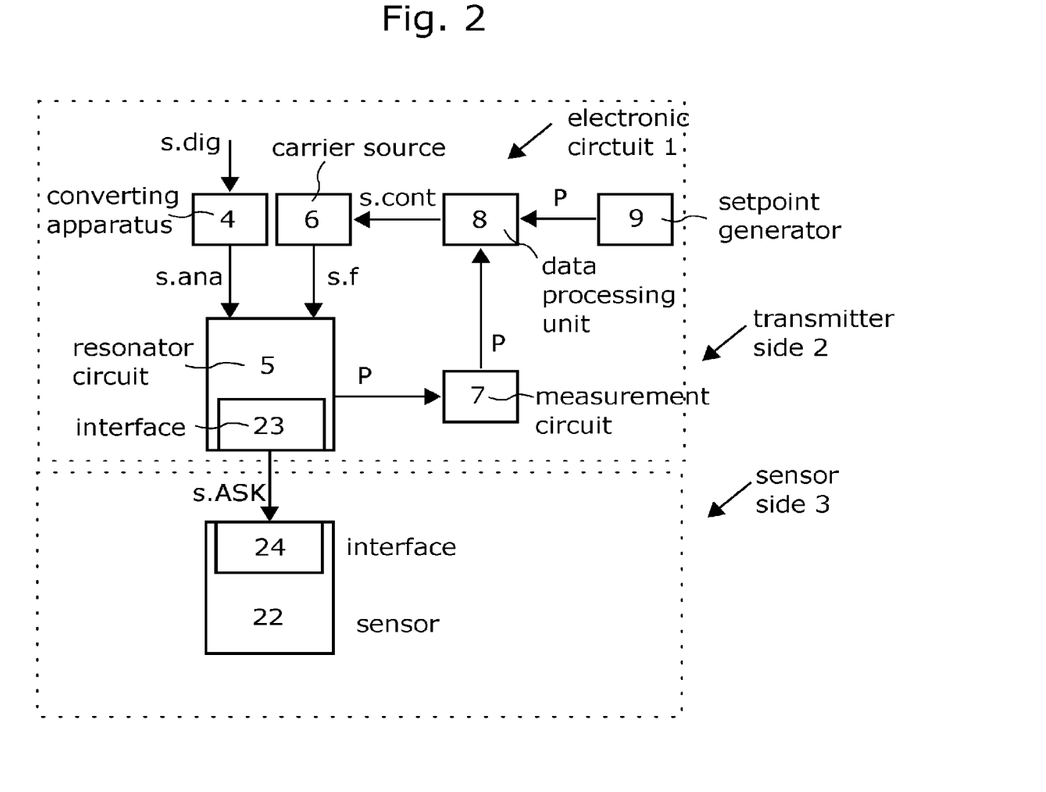
FIG. 2 is a schematic block diagram of the circuit of the invention.

The circuit of the invention in its totality bears the reference character 1 and is shown in FIG. 2 in the form of a schematic, block diagram. Circuit 1 is located on the transmitter side 2. Transmitter side 2 is connectable with the sensor-side 3 via the already mentioned, first interface 23 and second interface 24. First interface 23 is implemented as part of a resonator circuit 5, which is described in greater detail with reference to FIGS. 3 to 5.

Electronic circuit 1 includes the following components: converting apparatus 4, carrier source 6, resonator circuit 5 with first interface 23, measurement circuit 7 and data processing unit 8 with setpoint generator 9.

Fed to converting apparatus 4 are data, especially a digital data signal s.dig. In the following, all "signals" are referred to with a reference symbol bearing the prefix "s.". Converting apparatus 4 converts the data signal s.dig into an analog, wanted signal s.ana.

The carrier source 6 is a signal source, which generates a carrier signal s.f having a carrier frequency. Frequently selected as carrier signal is a sinusoidal signal. Besides a sinusoidal signal are, however, other signal forms, such as ones having a rectangular or triangular form, provide viable options. Especially, a (digital) output of the data processing unit 8 can be used, in which case a rectangular form results (see in this connection also below).

The resonator circuit merges the wanted signal s.ana with the carrier signal s.f to form the signal to be transmitted, the ASK-signal s.ASK. This ASK-signal is then transmitted via the first and second interfaces 23, 24 from the transmitter side 2 to the sensor-side 3.

A measurement circuit 7 measures the power P, thus especially the electrical current- and voltage level, of the ASK-signal s.ASK. The measurement circuit 7 forwards the measured value to a data processing unit 8. An option is that the measurement circuit 7 or also only parts of the measurement circuit 7 are implemented in the data processing unit 8. Especially calculation of the power can happen in the data processing unit 8. Data processing unit 8 can be embodied, in such case, as a microcontroller, microprocessor or the like. Data processing unit 8 must, in such case, be able to receive and to transmit signals, to execute (control-) algorithms and to deliver corresponding control signals.

Data processing unit 8 receives predetermined by the setpoint generator 9 the desired value of the power to be transmitted. An option is that the setpoint is stored in the data processing unit 8, e.g. in firmware. Also, a modifying of the value of the setpoint is another option effected, for example, by a suitable communication signal. The setpoint should thus be variable, i.e., depending on state or operating mode of the sensor 22 (thus the receiver of the power), another setpoint should be settable. A operating mode, "memory erase", "firmware change" or the like can, for example, require a higher power.

Data processing unit 8 controls with the measurement data of the measurement circuit 7 and the setpoint the carrier frequency of the carrier signal s.f based on a control signal s.cont. The manipulated variable is, thus, the carrier frequency. As is explained below, a smaller carrier frequency means an increasing of the electrical current in the resonator circuit 5 and therewith also in the interfaces 23, respectively 24 and therewith also in the sensor 22.

An essential characteristic of this control is that the value of the power is detected by the measurement circuit 7 and, in the case of deviation from its intended value (set value from the setpoint generator 9), the power is brought by appropriate interaction back to its intended value.

In designing the carrier source 6 for generating the carrier signal s.f, it is to be taken into consideration that, on the one hand, the adjustable frequency raster has sufficiently fine separations, in order to be able to set the optimal working point of the resonator circuit 5 sufficiently finely. On the other hand, the tuning range of the clock source must be sufficiently large, in order to be able to cover safely all expected extreme values of the frequency to be set in the context of piece variations and temperature drift.

An advantageous variant for producing the frequency is to utilize a constant frequency oscillator of high frequency $F0$ and via a programmable frequency divider with high divider of e.g. $n=200+/-20$ to generate a carrier frequency $f=F0/N$ with a tuning raster of $f*(1/N-1/(N+1))$ finely stepped by variation of N and corresponding to about a half percent of the carrier frequency. Another option is use of variable RC oscillators as clock source, especially in the power range below 20 mW. Alternatively used for the clock source can be a microcontroller, which internally has a tunable RC clock source or a constant frequency oscillator, which can be internally divided down with a programmable divisor to the desired carrier frequency. Especially the data processing unit 8 is capable of this. Alternatively to using a microcontroller for frequency control, another option is to construct an analog control loop, e.g. PID control loop, e.g. by means of an operational amplifier, whose output voltage is forwarded to a voltage controlled oscillator, a so-called VCO. The control occurs, in this case, purely analogly.

Typically, data are not continuously sent. In contrast, the sensor 22 is continuously supplied with energy. During the data transmission, no reliable control of the power is possible. A possible arrangement is to perform no frequency adjustments of the carrier signal s.f and to conduct no power measurements during the data transmission. A further advantage of this method is that in this way it can be excluded that during an ongoing communication a control action results in an undesired amplitude modulation in the carrier frequency, which erroneously could be interpreted as a change in the ASK signal.

Figure 3A:
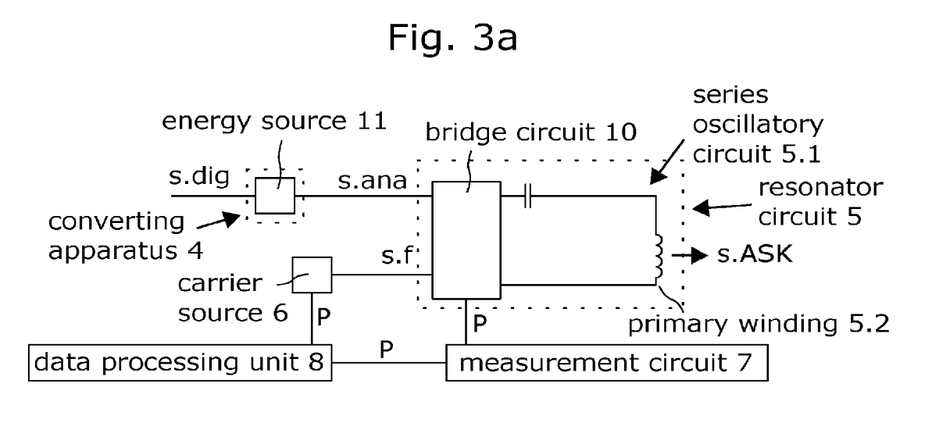
FIG. 3a is a first embodiment of the resonator circuit.
Figure 3B:
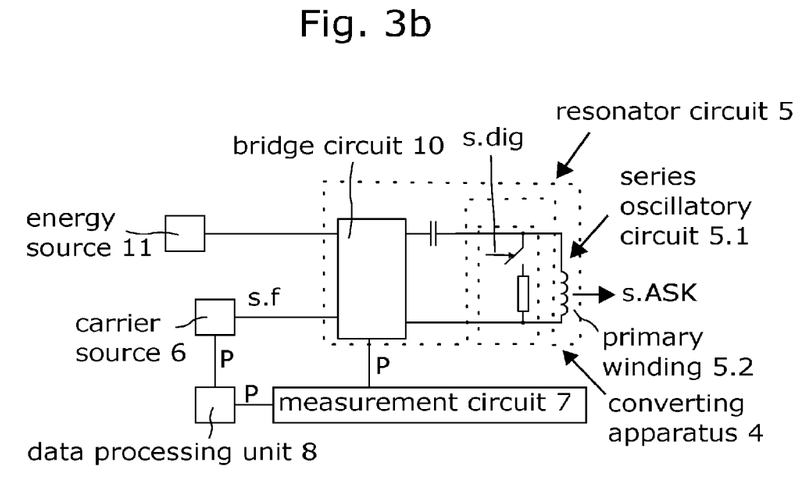
FIG. 3b is a variant of the first embodiment of the resonator circuit.

FIG. 3 shows a first embodiment of the resonator circuit 5 with a first variant in FIG. 3a and a second variant in FIG. 3b.

The heart of the resonator circuit 5 in FIG. 3a and FIG. 3b is a bridge circuit 10, especially a half- or full bridge. Preferably, a four quadrant controller is used. Those skilled in the art are acquainted with four quadrant controllers, so that such is not explained in detail here.

In a four quadrant controller, in each case, a pair of so called "high side transistors" is utilized, which can turn the energy supply to the output, and a pair of so called "low side transistors", which can switch the output to ground. In such case, the control signals are connected to the carrier source 6. As a result, two exactly opposite phase, rectangular signals of the carrier frequency are generated, to which the two connections of the series oscillatory circuit 5.1 are connected. The coil 5.2 forms, in such case, the primary winding and therewith the first interface 23.

In the form of embodiment of FIG. 3a, the bridge circuit 10 is, in such case, supplied by the signal s.ana both with energy as well as also by means of a data dependent modulating of the voltage s.ana also with the data signal to be transmitted. The conversion of the data signal into an ASK-signal occurs, in such case, in that an increasing of the input voltage of the bridge circuit leads to a voltage increase of the carrier frequency oscillation.

In the form of embodiment of FIG. 3b, the bridge circuit 10 is fed with energy with an approximately constant operating voltage and the modulation of the ASK signal occurs by connecting a network, e.g. a resistive network, to one of the components of the series oscillatory circuit 5.2. In the example of FIG. 3b, that is the coil. Dependent on the data signal s.dig, there results, thus, a stronger or less strong attenuation of the oscillatory circuit and therewith an amplitude modulation. For the attenuation of the oscillatory circuit, the exact position of the attenuating network is of lesser importance. It would also be possible in the example of FIG. 3b especially to shunt the series capacitor via the switch means. This holds analogously for the position of the attenuation network in the circuit of FIG. 5b The measuring of the power transmitted in the coil 5.2 to the secondary side can occur by metrologically registering the power converted in the bridge circuit 10. This can be ascertained using the example of FIG. 3a e.g. by multiplying the input voltage s.ana used for the energy supply and the voltage in this line falling across a shunt resistor (proportional to the electrical current). Advantageously, the shunt resistor can also be inserted into the ground path of the switch means of the bridge circuit 10, since a measuring of a small voltage difference is, as a rule, achieved more simply in the case of a small direct voltage level then in the case of a greater direct voltage level.

The application of a microcontroller as clock source 6 is because of this especially advantageous, because via the multiply integrated analog-digital converter a simple ascertaining of the supply voltage of the bridge circuit is achieved likewise as a digital conversion of the voltage falling across a shunt resistor, respectively a digital conversion of the electrical current. These two sub signals can then advantageously be combined by multiplication to form a power index, which serves as input signal of the control algorithm that controls the frequency of the carrier signal s.f. The multiplication required for the power determination would be implementable in purely analog built up control circuits only with significantly greater effort.

A characteristic of the resonator circuits 5 of FIGS. 3a/b is that the voltage on the first interface 23 (primary winding) has symmetric positive and negative half-waves. The circuit has therewith advantages, when at the second interface 24, for instance, equally much power should be removed from the negative- and positive half-waves of the voltage, e.g. when a sensor should be operated, which requires a bipolar power supply and the two polarities are, for instance, equally strongly utilized. Advantageous further is that the oscillatable system is simple to calculate and contains besides the primary winding only a capacitor.

Figure 4A:
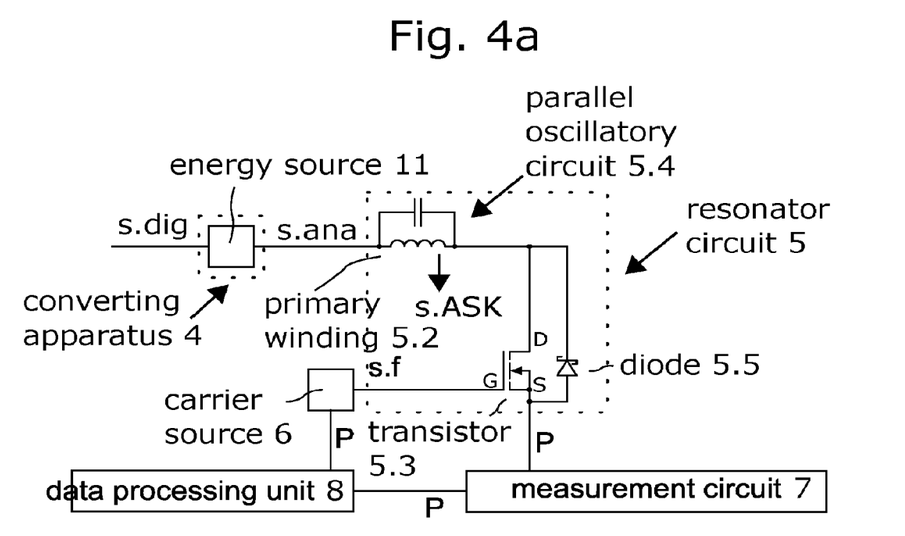
FIG. 4a is a second embodiment of the resonator circuit.
Figure 4B:
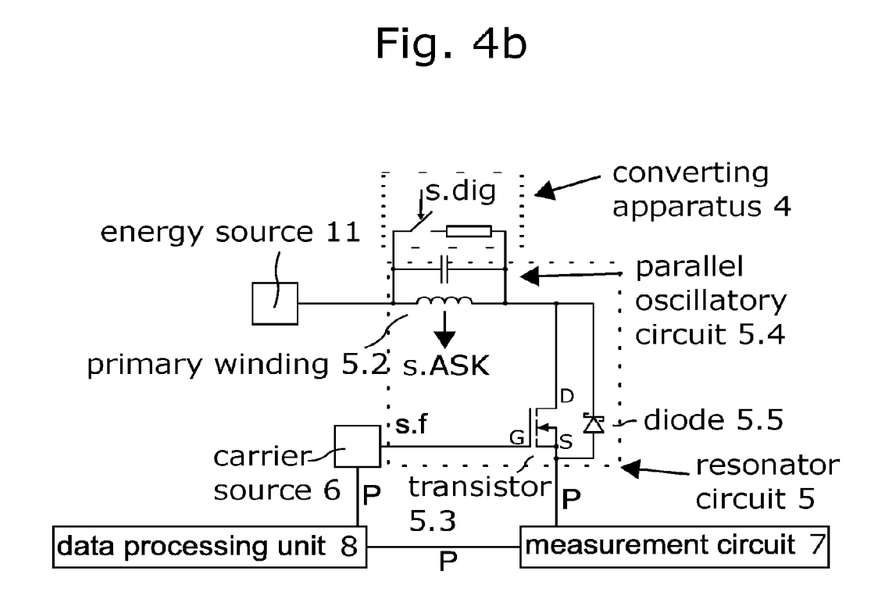
FIG. 4b is a variant of the second embodiment of the resonator circuit.

FIG. 4 shows a second embodiment of the resonator circuit 5 with a first variant in FIG. 4a and a second variant in FIG. 4b.

In this form of embodiment, the primary winding 5.2 is connected with a capacitor to form a parallel oscillatory circuit 5.4. The first input of the parallel oscillatory circuit 5.4 is connected with the converting apparatus 4 (FIG. 4a), respectively parallel to the parallel oscillatory circuit 5.4 (FIG. 4b). The second input of the parallel oscillatory circuit 5.4 is connected to the drain-connection D of a transistor 5.3. If the transistor 5.3 is periodically closed via the gate-connection G, a periodic alternating voltage signal arises on the primary winding 5.2. In this topology, efficiency can be improved by adding a diode 5.5 with a low forward voltage drop, e.g. a Schottky diode. The power measuring can occur corresponding to the method described in connection with FIG. 3 by measuring the power converted in the resonator circuit. A shunt resistor used for electrical current measurement would advantageously be installed between the source-connection of the transistor 5.3 and ground. As an alternative for electrical current measurement at the source-connection S, the electrical current measurement can also occur after the converting apparatus 4. Also, electrical current can be measured on the source-connection S and voltage on the amplifier 11 and, vice versa. An electrical current measurement can occur, in such case, for instance, via a shunt. The power is then calculated in the data processing unit 8. The power is thus determined and the ascertained value is forwarded to the data processing unit 8. This controls the power transmitted by changing the carrier frequency s.f at the carrier source 6. The carrier source can, for instance, also be implemented by the data processing unit 8 (e.g. as digital output). The carrier signal s.f is then a rectangular signal, which is converted by the resonator circuit 5 into an approximate sinusoidal signal.

The difference between FIG. 4a and FIG. 4b lies in the implementing of the data modulation within the converting apparatus.

In FIG. 4a the converting apparatus 4 is embodied as an energy source 11. The energy source 11 converts the digital data signal s.dig into an analog wanted signal s.ana. In such case, a high-level (logic "1") assumes, for example, a voltage of 2.5 V and a low-level (logic "0") assumes, for example, a 10% smaller voltage. The data signal s.dig thus modulates the voltage of the energy source 11. This signal is then amplified by the energy source 11, in order that on its output this voltage is available with sufficient power, in order therewith to supply the resonator circuit 5. In a form of embodiment, the energy source 11 is embodied as a linear amplifier. However, also a class-D amplifier is an option, as is a direct voltage converter. Also, an amplifier such as disclosed in the as yet unpublished German patent application DE 10 2012 110 310 can be used.

In FIG. 4b, the conversion of digital data signal s.dig into an analog signal occurs by load modulation. Connected to the input of the resonator circuit 5 is an energy source 11, which delivers an essentially constant voltage. The data signal s.dig closes a switch, whereby at least one impedance (in the example symbolized by a resistor) is connected, and the voltage level sinks correspondingly.

Notable in connection with FIG. 4a/b is that the shown switching of the oscillatory circuit capacitor out of the parallel oscillatory circuit 5.4 in the context of the alternating voltage is largely equivalent to a connecting of the capacitor to ground. Regarding the carrier frequency s.f, the output signal of the energy supply 11 can be considered as constant direct voltage, so that the there connected side of the capacitor can alternatively also be switched to ground. The same holds for the switching of the parallel oscillatory circuit in FIG. 5a and FIG. 5b.)

Figure 5A:
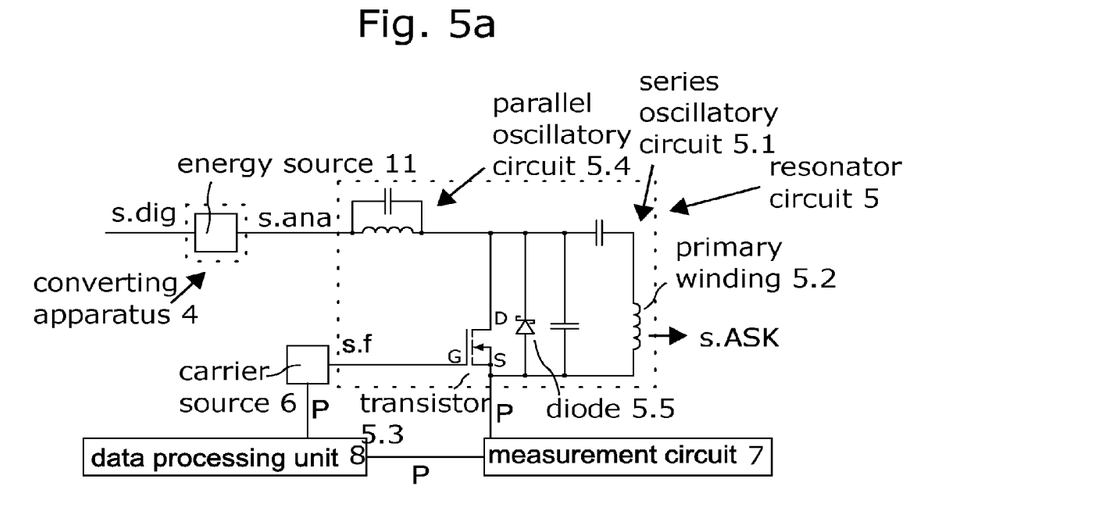
FIG. 5a is a third embodiment of the resonator circuit.
Figure 5B:
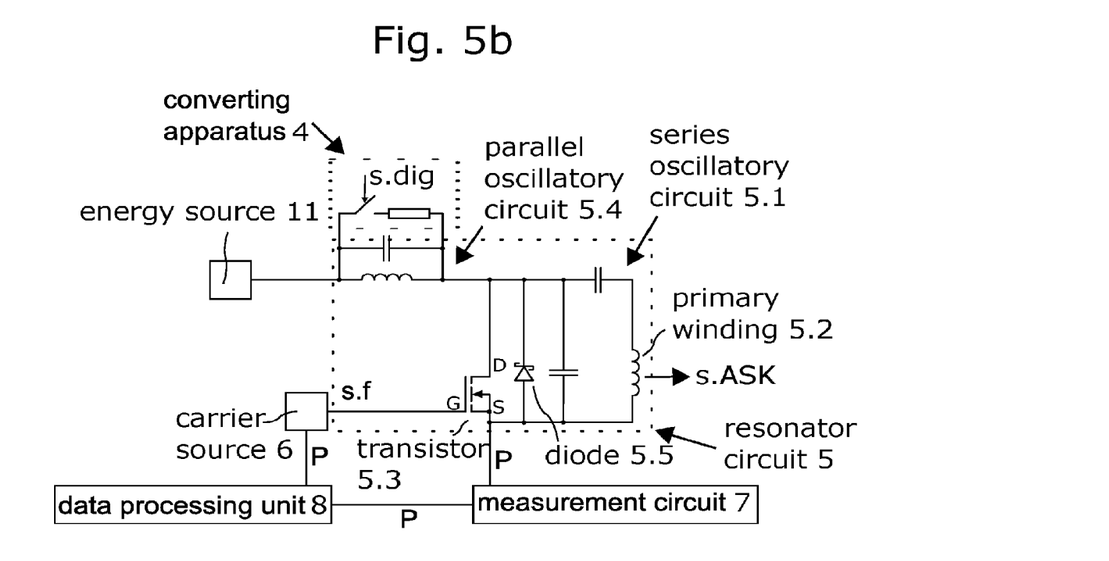
FIG. 5b is a variant of the third embodiment of the resonator circuit.

FIG. 5 shows a third embodiment of the resonator circuit 5 with a first variant in FIG. 5a and a second variant in FIG. 5b.

The resonator circuit 5 is embodied as a double oscillatory circuit. The oscillatable system here is formed of a series oscillatory circuit 5.1 and a parallel oscillatory circuit 5.4, which are connected together. Series oscillatory circuit 5.1 and parallel oscillatory circuit 5.4 possess, in each case, at least one capacitor and one coil. The exciting to oscillation occurs via a switch element 5.3, for example, a transistor. A diode 5.3, e.g. a Schottky diode, connected parallel to the switch element 5.3 can increase the efficiency. The coil 5.2 is the primary winding, part of the series oscillatory circuit 5.1 and forms the first interface 23, by which the ASK-signal s.ASK is transmitted Otherwise, the circuits in FIG. 5a, respectively FIG. 5b, are constructed similarly to the circuits in FIG. 4a, respectively FIG. 4b. The digital data signal s.dig is, in each case, led to the converting apparatus 4. The conversion happens either via an amplifier 11 (FIG. 5a, see text for FIG. 4a) or by load modulation (FIG. 5b, see text for FIG. 4b).

The measuring of the power happens also here via the measurement circuit 7 at the source-connection S of the transistor 5.3 or directly after the amplifier 11. Also, electrical current can be measured at the source-connection S and voltage at the amplifier 11 and, vice versa. An electrical current measurement can occur in such case, for instance, via a shunt. The power is then calculated in the data processing unit 8.

After the power measuring by the measurement circuit 7, a data processing unit 8 controls the carrier frequency of the carrier source 6 and the carrier frequency is fed to the gate-connection G of the transistor 5.3.

Field effect transistors are used in the examples. One skilled in the art is, however, also able to use bipolar transistors or other switch means.

The circuits shown in FIGS. 4 and 5 produce on the primary winding 5.2 an asymmetric voltage curve, which provides advantages, when energy on the second interface 24 should essentially only be removed by the sensor-side 3 in one of the two half waves.

Regarding the balance between energy available on the secondary side in the positive and negative half-waves, the circuit in FIG. 5 forms, in such case, a compromise between the two circuits of FIGS. 3 and 4. In the circuit of FIG. 5, energy can be removed in both half waves, wherein the one is, however, clearly preferably. This topology is advantageous for the operation of sensors on the secondary side, which require both a negative as well as also a positive supply voltage but burden one of the two polarities more strongly.

The topologies of FIG. 4 and FIG. 5 have, in such case, together the advantage that only a single transistor is sufficient as switch means and the switch means can be operated without a complex drive circuit.

Common to all resonator circuits 5 of FIGS. 3 to 5 is that it is possible by changing the carrier frequency to increase or decrease the power sent from the primary winding 5.2 (=interface 23) to the secondary winding (=interface 24). It is to be heeded that in the design of the resonator circuit 5 the efficiency in the tuning range should remain approximately constant. Then the power removed from the primary side and directly available to the secondary side can be deduced.

The amplitude of the ASK-signal s.ASK changes, in such case, linearly with the wanted signal s.ana. Via a variation of the wanted signal s.ana, it is, thus, possible to achieve a voltage change of the alternating voltage component in the case of the ASK-signal s.ASK to be transmitted. This effect can be utilized to modulate data onto the ASK-signal s.ASK by means of an amplitude modulation.

If the resonator circuit 5 is operated with higher levels of the wanted signal s.ana, then higher alternating voltage amplitudes s.ASK are set on the primary and secondary windings. If a smaller voltage is placed on the input of the resonator circuit 5 by the energy source 11, then smaller alternating voltage amplitudes s.ASK will be on the primary and secondary windings. The alternating voltage modulation can, thus, be traced back to a direct voltage modulation.

The modulating of the primary coil voltage via an energy source 11 in the form of an amplifier circuit (FIG. 3a, FIG. 4a and FIG. 5a) with logic level dependent output voltage has the advantage that therewith better efficiencies can be achieved than with alternative modulation methods, such as a resistive attenuation of the primary winding (FIG. 3b, FIG. 4b and FIG. 5b). Also, with this method, the influences of example variations are smaller. If e.g. a 10% modulation amplitude is required, this can be implemented simply and precisely by 10% reduction of the input direct voltage on the input of the resonator circuit 5, independently of example variations of the components. This property depends also on the fact that the resonance determining voltage levels can be considered as linear and increase in proportion to the direct voltage provided on the input.

As already mentioned, the transmitter side 2 is connected with the sensor-side 3 via the interfaces 23, 24. It is to be heeded that there is no capacitive coupling of the electronic components on transmitter side 2 with conductive elements (e.g. the secondary winding) of the sensor-side 3. In the case of presence of usual electromagnetic disturbance fields in industrial applications, it is possible that between the components on the transmitter side 2 and the sensor-side 3 voltage differences of a number of kilovolt can exist (e.g. due to electrostatic charges), which especially in the case of electrostatic fields can also abruptly collapse. These voltage differences lead to the formation of electrical field lines, which can extend between transmitter-side 2 and sensor-side 3 and which bring about capacitive displacement currents.

Figure 6A:
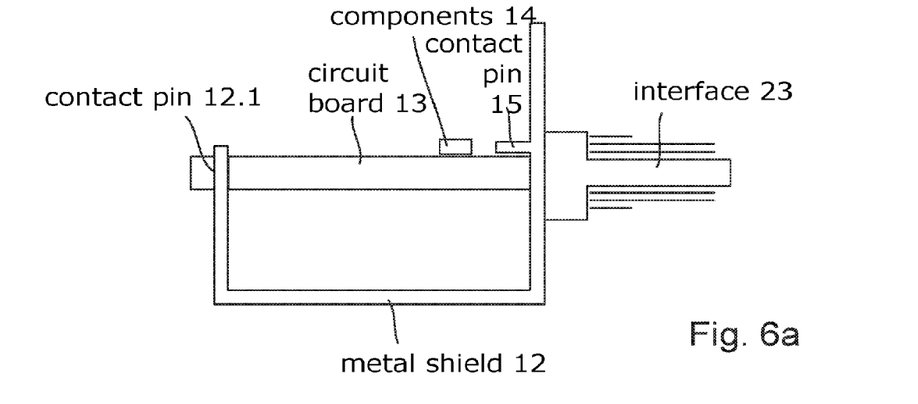
FIG. 6a is an arrangement of the circuit of the invention with the shield arrangement of FIG. 6b.
Figure 6B:
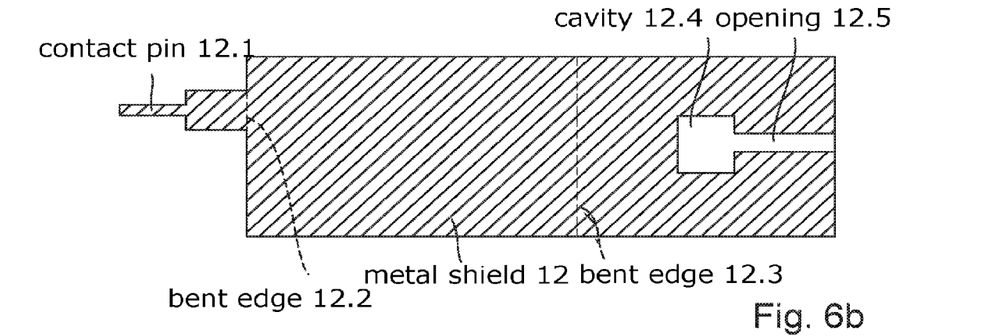
FIG. 6b is a first embodiment of a shield arrangement for shielding the circuit of the invention against external influences.
Figure 6C:
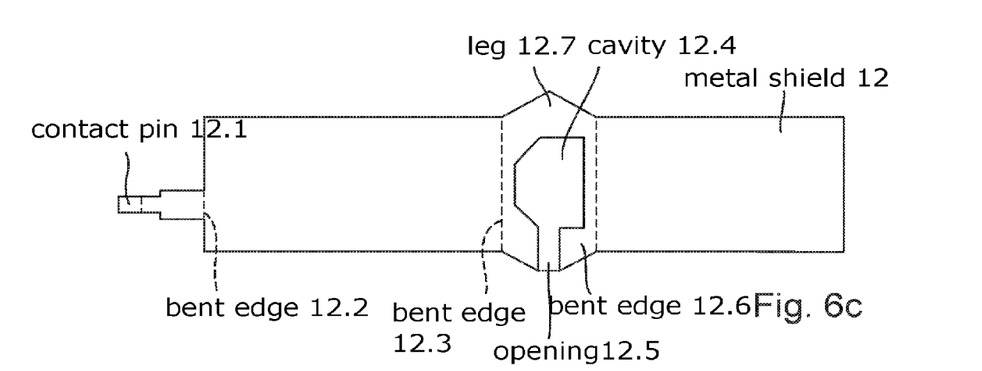
FIG. 6c is a second embodiment of a shield arrangement for shielding the circuit of the invention against external influences.

FIGS. 6a-c show because of this a metal shield 12. FIG. 6a shows the metal shield 12 arranged for shielding a circuit board 13. Located on the circuit board 13 are the components 14 of the transmitter side 2. First interface 23 is also arranged on the circuit board 13. Likewise connected to the circuit board 13 is a connection cable, which connects the transmitter side 2 with, for example, a transmitter 21.

In advantageous manner, the metal shield 12 is connected conductively with a ground potential. Alternatively, the metal shield 12 can be connected with an in given cases present, cable shield of the cable connecting circuit board 13 to transmitter 21. If the metal shield 12 is connected in such a manner conductively with a ground potential, it acts as an equipotential surface for forming the electrical fields. The consequence is that the electrical field lines, which connect the sensor-side 3 with the transmitter side 2, end predominantly on the metal shield 12 and it is therewith prevented that field lines extend between electronic components 14 of the transmitter side 2 and conductive surfaces of the sensor-side 3. In other words, the metal shield 12 acts as a "lightning rod", which, in given cases, drains disturbance currents via a defined disturbance current path to a ground potential and therewith prevents that disturbance currents flow at other locations.

FIG. 6b will now be explained in greater detail. The first interface 23, thus the primary winding, is connected via contact pins 15 conductively with a circuit card 13. The rod-shaped primary winding 23 is inserted through an opening 12.4 in the metal shield 12. A contact pin 12.1 of the metal shield 12 is inserted through an opening of the circuit board 13 and soldered there. Two bent edges 12.2 and 12.3 are indicated as lines. The metal shield 12 includes a slot-like opening 12.5. If the opening 12.5 would be missing, the shield would act on a primary winding 23 inserted through the necessary cavity 12.4 like a short-circuited and especially low ohmic, single winding, i.e. the shield 12 would cause a short-circuiting of the primary winding 23. As a consequence, the resonator circuit 5 would no longer function. The short-circuiting would be produced by the fact that annular electrical currents would flow around the cavity 12.4 in the metal shield 12. If the metal shield 12.4 is embodied, however, in such a manner that a slot shaped opening 12.5 suppresses these annular electrical currents by interrupting their path, then the inductive properties of the transformer system are not significantly influenced. An option is to turn the direction of the slot 12.5 by 90° such as in shown FIG. 6c.

Examples of material for metal shield 12 are especially copper alloys, especially CuBe and CuSn-alloys. Especially advantageous is production of the metal shield as a blanked, bent, sheet-metal part, in given cases, however, also as an etch or laser cut part with selective material weakening at the location of the bent edges.

An improving of the shielding properties is possible, when the expanse of the sheet metal is increased, e.g. such as shown in FIG. 6c, in such a manner that it contains a third bent edge 12.6 and an additional leg 12.7, which covers the circuit board 13 also on its upper side.

Moreover, it is advantageous, when the ground connection of the first interface 23 lies "outwardly" on the coil, while the second connection lies "internally". This is sketched schematically in FIG. 6a. The primary winding 23 there is composed of wire wound as two full plies and one partially filled ply. In this way, it can be assured that the external ply connected with the ground potential is shielded against a direct capacitive in-coupling of a disturbance signal.

The invention claimed is:

1. An electronic circuit for transmitting an ASK-signal, wherein the ASK-signal transmits data and energy between a first side having a first interface, and a second side having a second interface corresponding to the first interface, of a measuring device, said first interface and said second interface transmit data and energy, and said first interface and said second interface are galvanically separated interfaces, comprising:

a converting apparatus for transforming a digital data signal including the data into an analog useful signal;
a carrier source for producing a carrier signal having a carrier frequency;
a resonator circuit for merging the carrier signal with the useful signal to form the ASK-signal with an amplitude, wherein the useful signal determines the amplitude of the ASK-signal;
a measurement circuit for measuring the power of the ASK-signal, wherein said power corresponds to said energy to be transmitted; and
a data processing unit, which controls the carrier frequency of the carrier signal, wherein a controlled variable is the measured power of the ASK-signal, and a manipulated variable is the carrier frequency, whereby the data processing unit controls the transmission of the ASK-signal, wherein:
said resonator circuit is excited to execute periodic oscillations by the carrier signal; and
the ASK-signal includes the useful signal and the periodic oscillations.

2. The electronic circuit as a claimed in claim 1, wherein: said data processing unit acts as said carrier source.

3. The electronic circuit as claimed in claim 2, wherein: said data processing unit suspends control action while data are being sent by omitting frequency adjustment of the carrier signal and omitting power measurements when data are being sent.

4. The electronic circuit as claimed in claim 1, wherein: the setpoint of the controlled variable power is variable.

5. The electronic circuit as claimed in claim 1, wherein: said converting apparatus is an amplifier and the data determines the amplification.

6. The electronic circuit as claimed in claim 1, wherein: said converting apparatus is a load modulation circuit having at least one switch means and at least one impedance addable by the switch means and the data determines the switching of the switching means.

7. The electronic circuit as claimed in claim 1, wherein: said resonator circuit includes at least:
a bridge circuit comprising a half or full bridge; and
a series LC circuit, said series LC circuit is connected with said bridge circuit;
said series LC circuit corresponds to the first interface; and
the useful signal and the carrier signal are fed to said bridge circuit.

8. The electronic circuit as claimed in claim 7, wherein: said bridge circuit comprises a four quadrant controller.

9. The electronic circuit as claimed in claim 1, wherein: said resonator circuit includes at least:
a parallel LC circuit having an input and an output, said the parallel LC circuit corresponds to the first interface; and
a transistor, having a gate-connection, a drain-connection and a source-connection, wherein:
the useful signal is fed to the input of said parallel LC circuit;
the output of said parallel LC circuit is connected with the drain-connection; and
the gate-connection is fed the carrier signal.

10. The electronic circuit as claimed in claim 1, wherein said resonator circuit includes at least:
a parallel LC circuit with an input and an output;
a transistor, having a gate-connection, a drain-connection and a source-connection; and a series LC circuit;

said series LC circuit corresponds to the first interface;

the useful signal is fed to the input of said parallel LC circuit;

the output of said parallel LC circuit is connected with said drain-connection;

said series LC circuit connects said drain-connection with said source-connection; and said gate-connection is fed the carrier signal.

11. A measuring device, comprising:

an electronic circuit for transmitting an ASK-signal, wherein the ASK-signal transmits data and energy between a first side having a first interface, and a second side having a second interface corresponding to the first interface, of a measuring device, said first interface and said second interface transmit data and energy, and said first interface and said second interface are galvanically separated interfaces, comprising:

a converting apparatus for transforming a digital data signal including the data into an analog useful signal;

a carrier source for producing a carrier signal having a carrier frequency;

a resonator circuit for merging the carrier signal with the useful signal to form the ASK-signal with an amplitude, wherein the useful signal determines the amplitude of the ASK-signal;

a measurement circuit for measuring the power of the ASK-signal, wherein said power corresponds to said energy to be transmitted; and a data processing unit, which controls the carrier frequency of the carrier signal, wherein a controlled variable is the measured power of the ASK-signal, and a manipulated variable is the carrier frequency; and hence the data processing unit controls the transmission of the ASK-signal, wherein:

said resonator circuit is excited to execute periodic oscillations by the carrier signal; and the ASK-signal includes the useful signal and the periodic oscillations.

12. The measuring device as claimed in claim 11, wherein:

the measuring device includes a superordinated unit and a consumer, said superordinated unit is connected with said consumer via the first interface and the second interface.

13. The measuring device as claimed in claim 12, wherein: the superordinated unit is a transmitter.

14. The measuring device as claimed in claim 12, wherein: the consumer is a sensor.

15. A method for transmitting an ASK-signal between a first side and a second side of a measuring device, wherein the ASK-signal transmits data and energy, comprising the steps of:

converting a digital data signal including the data into an analog useful signal;

producing a carrier signal having a carrier frequency;

merging the carrier signal with the useful signal to form the ASK-signal with an amplitude, wherein periodic oscillations are produced by the carrier signal, and the ASK-signal includes the useful signal and the periodic oscillations; and the amplitude of the ASK-signal is determined by the useful signal; and transmitting the ASK-signal, wherein:

the power of the transmission is determined and the transmission of the ASK-signal is controlled, wherein said power corresponds to said energy to be transmitted; and a controlled variable is the measured power of the ASK-signal, and a manipulated variable is the carrier frequency.

16. The method as claimed in claim 15, wherein:

the useful signal is generated by an amplifier and the amplification is predetermined by the data.

17. The method as claimed in claim 15, wherein:

the useful signal is generated by a switchable load and the switching is predetermined by the data.

* * * * *